（12）United States Patent
Mechlenburg et al.

(10) Patent No.: US 9,901,692 B2
(45) Date of Patent: Feb. 27, 2018

(54) SYSTEM AND METHOD FOR TREATING LUNG DISEASE USING POSITIVE PRESSURE AIRWAY SUPPORT

(75) Inventors: Douglas Mechlenburg, Murrysville, PA (US); Richard J. Coldren, New Stanton, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1244 days.

(21) Appl. No.: 13/131,902

(22) PCT Filed: Nov. 21, 2009

(86) PCT No.: PCT/IB2009/055259
§ 371 (c)(1),
(2), (4) Date: May 31, 2011

(87) PCT Pub. No.: WO2010/070498
PCT Pub. Date: Jun. 24, 2010

(65) Prior Publication Data
US 2011/0232643 A1 Sep. 29, 2011

Related U.S. Application Data

(60) Provisional application No. 61/139,077, filed on Dec. 19, 2008.

(51) Int. Cl.
*A61M 16/00* (2006.01)
*A61B 5/085* (2006.01)
(Continued)

(52) U.S. Cl.
CPC .......... *A61M 16/026* (2017.08); *A61B 5/085* (2013.01); *A61M 16/0069* (2014.02);
(Continued)

(58) Field of Classification Search
CPC .............. A61M 16/00; A61M 16/0003; A61M 16/0051; A61M 2016/0027;
(Continued)

(56) References Cited

U.S. PATENT DOCUMENTS 4,802,492 A * 2/1989 Grunstein .............. A61B 5/085
600/533
5,038,769 A * 8/1991 Krauser ................ A61M 15/00
128/203.27
(Continued)

FOREIGN PATENT DOCUMENTS

JP 2008110221 A 5/2008
JP 2010517701 A 5/2010
(Continued)

*Primary Examiner* — Colin W Stuart

(57) ABSTRACT

A method of treating lung disease, such as asthma or COPD, is provided that includes determining a parameter indicative of a patient's pulmonary mechanics (such as, without limitation, airway resistance or lung compliance), and delivering positive pressure support to the airway of the patient, wherein the pressure level (which may be constant or variable) of the positive pressure support during at least a portion of the inspiratory phase of the patient is determined based on the determined parameter.

25 Claims, 9 Drawing Sheets

(51) Int. Cl.
    *A61M 11/00* (2006.01)
    *A61M 15/00* (2006.01)
    *A61M 16/20* (2006.01)

(52) U.S. Cl.
    CPC ........ *A61M 16/021* (2017.08); *A61M 16/022* (2017.08); *A61M 16/024* (2017.08); *A61M 11/00* (2013.01); *A61M 15/00* (2013.01); *A61M 16/0003* (2014.02); *A61M 16/0006* (2014.02); *A61M 16/202* (2014.02); *A61M 2016/003* (2013.01); *A61M 2016/0027* (2013.01); *A61M 2016/0039* (2013.01); *A61M 2230/46* (2013.01)

(58) Field of Classification Search
    CPC .... A61M 2016/003; A61M 2016/0021; A61M 2016/0039; A61M 2016/0036; A61M 16/021; A61M 16/022; A61M 16/024; A61M 16/026
    USPC ............ 128/204.23, 200.24, 203.12, 203.14, 128/203.15, 204.18, 204.21
    See application file for complete search history.

(56) References Cited

U.S. PATENT DOCUMENTS

| | | |
|---|---|---|
| 5,148,802 A | 9/1992 | Sanders |
| 5,239,995 A | 8/1993 | Estes et al. |
| 5,297,543 A | 3/1994 | Larson et al. |
| 5,313,937 A | 5/1994 | Zdrojkowski |
| 5,433,193 A | 7/1995 | Sanders et al. |
| 5,535,738 A | 7/1996 | Estes et al. |
| 5,881,724 A | 3/1999 | Graetz et al. |
| 6,257,234 B1 | 7/2001 | Sun |
| 6,532,960 B1 | 3/2003 | Yurko |
| 6,609,517 B1 | 8/2003 | Estes et al. |
| 6,640,806 B2 | 11/2003 | Yurko |
| 6,837,242 B2 | 1/2005 | Younes |
| 8,746,247 B2 * | 6/2014 | Mechlenburg ........... 128/204.21 |
| 2002/0026941 A1 * | 3/2002 | Biondi et al. ........... 128/204.21 |
| 2004/0097821 A1 | 5/2004 | Blomberg et al. |
| 2006/0000472 A1 | 1/2006 | Fenton et al. |
| 2006/0000475 A1 | 1/2006 | Matthews et al. |
| 2006/0201500 A1 | 9/2006 | Von Hollen et al. |
| 2007/0000494 A1 * | 1/2007 | Banner et al. ........... 128/204.23 |
| 2007/0089745 A1 | 4/2007 | Gabriel et al. |
| 2007/0272241 A1 * | 11/2007 | Sanborn et al. ........ 128/204.23 |
| 2008/0202528 A1 | 8/2008 | Carter et al. |
| 2008/0236582 A1 * | 10/2008 | Tehrani .................... 128/204.22 |
| 2008/0257337 A1 | 10/2008 | Denyer et al. |

FOREIGN PATENT DOCUMENTS

| | | |
|---|---|---|
| WO | 2007134099 A2 | 11/2007 |
| WO | 2008100859 A2 | 8/2008 |

\* cited by examiner

SYSTEM AND METHOD FOR TREATING LUNG DISEASE USING POSITIVE PRESSURE AIRWAY SUPPORT

This patent application claims the priority benefit under 35 U.S.C. § 119(e) of U.S. Provisional Application No. 61/139,077 filed on Dec. 19, 2008, the contents of which are herein incorporated by reference.

The present invention relates to systems and methods for treating lung diseases such as asthma, COPD or other lung diseases that effect the airways, and in particular to systems and methods for treating such lung diseases using positive pressure airway support.

Asthma is a chronic lung disease that affects a person's bronchial tubes, also known as airways, which are the tubes that carry air into and out of the lungs. People that have asthma have airways that are inflamed as a result of swelling and the production of excess mucus. The airways of people that have asthma are also overly sensitive to things like exercise, dust, or cigarette smoke. This over-sensitivity causes the smooth muscle that surrounds the airways to tighten up when a person with asthma exercises or breathes such substances in. The combination of airway inflammation and muscle tightening narrows the airways and makes it difficult for air to move through them. As a result, people that have asthma experience recurring periods of wheezing, chest tightness, shortness of breath, and coughing, commonly called asthma attacks.

Typically, asthma is treated with medication in either or both of the following two ways. The first way employs what are commonly known as rescue medications. Rescue medications are administered as needed to immediately stop the symptoms of an acute attack. The second way attempts to manage the asthma and prevent attacks from occurring using what are commonly known as controller medications. Such controller medications are typically taken daily regardless of whether an attack has occurred and attempt to treat the airway inflammation associated with asthma.

While the use of medication for the treatment of asthma has proven to be effective in many cases, some people do not completely respond to medication and/or suffer from adverse side effects. In addition, in general, most physicians and/or asthma sufferers prefer to utilize the minimum medication dose required to be effective. Thus, there is always a need for additional therapy methods to be used in conjunction with and/or in place of (at least partially) medication to treat asthma and/or other lung diseases such as COPD that effect the airways.

In one embodiment, a method of treating lung disease, such as asthma or COPD, is provided that includes determining a parameter indicative of a patient's pulmonary mechanics (such as, without limitation, airway resistance or lung compliance), and delivering positive pressure support to the airway of the patient, wherein the pressure level (which may be constant or variable) of the positive pressure support during at least a portion of the inspiratory phase of the patient is determined based on the determined parameter. In one particular implementation, the pressure level of the positive pressure support during at least a portion of the inspiratory phase includes a peak pressure, and a second pressure level (which may be constant or variable) of the positive pressure support during at least a portion of an expiratory phase of the patient is below the peak pressure. Preferably, the second pressure level is also determined based on the determined parameter. In addition, the determining step may be performed prior to the delivering step, or, alternatively, the determining step may be performed during the delivering step.

In one particular embodiment, the invention provides a method of treating lung disease, such as asthma or COPD, that includes determining a parameter indicative of a patient's pulmonary mechanics, such as upper airway resistance or lung compliance, and delivering bi-level positive pressure support to an airway of the patient. The bi-level positive pressure support has an inspiratory positive airway pressure (IPAP) level and an expiratory positive airway pressure (EPAP) level, wherein one or both of the IPAP level and the EPAP level are determined based on the determined parameter.

In another embodiment, the invention provides a pressure support system for treating lung disease, such as asthma or COPD, that includes a pressure generating system adapted to produce a flow of breathing gas, a patient circuit operatively coupled to the pressure generating system to deliver the flow of breathing gas to an airway of a patient, and a controller operatively coupled to the pressure generating system. The controller is adapted to determine a parameter indicative of the patient's pulmonary mechanics and to control the pressure generating system to deliver the flow of breathing gas to the patient at a pressure level during at least a portion of an inspiratory phase of the patient, wherein the pressure level is determined based on the determined parameter. On one particular embodiment, the pressure level of the positive pressure support during at least a portion of the inspiratory phase includes a peak pressure, and the controller is adapted to control the pressure generating system to deliver the flow of breathing gas to the patient at a second pressure level during at least a portion of an expiratory phase of the patient that is below the peak pressure. Preferably, the second pressure level is also determined based on the determined parameter. The controller may be adapted to determine the parameter prior to the controlling of the pressure generating system, or, alternatively, the controller is adapted to determine the parameter during the controlling of the pressure generating system.

In another particular embodiment, the invention provides a pressure support system for treating lung disease, such as asthma or COPD, that includes a pressure generating system adapted to produce a flow of breathing gas, a patient circuit operatively coupled to the pressure generating system to deliver the flow of breathing gas to an airway of a patient, and a controller operatively coupled to the pressure generating system. The controller is adapted to determine a parameter indicative of the patient's pulmonary mechanics, such as upper airway resistance or lung compliance, and to control the pressure generating system to deliver the flow of breathing gas to the patient at an inspiratory positive airway pressure (IPAP) level during at least a portion of an inspiratory phase of the patient and deliver the flow of breathing gas to the patient at an expiratory positive airway pressure (EPAP) level during at least a portion of an expiratory phase of the patient. One or both of the IPAP level and the EPAP level are determined based on the determined parameter.

In another embodiment, the invention provides a method of treating lung disease, such as asthma or COPD, that includes (a) delivering a first bi-level positive pressure support at a predetermined baseline IPAP/EPAP differential for a first number of respiratory cycles, (b) determining a parameter indicative of the patient's pulmonary mechanics, such as upper airway resistance or lung compliance, and (c) determining that the determined parameter is outside of a predetermined baseline range. The method further includes (d) increasing the IPAP/EPAP differential to a current IPAP/EPAP differential, (e) delivering a second bi-level positive pressure support at the then current IPAP/EPAP differential for a second number of respiratory cycles, and (f) re-determining the parameter. Finally, in a step (g), the method includes repeating steps (d), (e) and (f) one or more times until either it is determined that the then current re-determined parameter is within the baseline range or that the then current IPAP/EPAP differential is equal to a predetermined maximum differential.

In one particular embodiment, if it is determined in step (g) that the then current IPAP/EPAP differential is equal to the predetermined maximum differential, the method further comprises notifying the patient to begin using asthma medication and continuing to provide the second bi-level positive pressure support at the then current IPAP/EPAP differential. Alternatively, if it is determined in step (g) that the then current IPAP/EPAP differential is equal to the predetermined maximum differential, the method further comprises automatically providing asthma medication to the patient while continuing to provide the second bi-level positive pressure support at the then current IPAP/EPAP differential, using, for example, a medication delivery device that is coupled to the patient circuit being used by the patient.

In yet another particular embodiment, if it is determined in step (g) that the then current re-determined parameter is within the baseline range, the method further comprises steps of (h) decreasing the then current IPAP/EPAP differential to a decreased level, (i) delivering a third bi-level positive pressure support at the decreased level for a third number of respiratory cycles, (j) re-determining the parameter, and (k) repeating steps (h), (i) and (j) one or more times until either it is determined that the then current re-determined parameter is outside of the baseline range or that the then current decreased level is equal to the baseline level. If it is determined in step (k) that the then current re-determined parameter is outside of the baseline range, the method repeats steps (d), (e), (f) and (g). Alternatively, if it is determined in step (k) that the then current re-determined parameter is not outside the baseline range and the then current decreased level is equal to the baseline level, the method further includes continuing to provide the third bi-level positive pressure support at the baseline level.

Therefore, it should now be apparent that the invention substantially achieves all the above aspects and advantages. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

The accompanying drawings illustrate presently preferred embodiments of the invention, and together with the general description given above and the detailed description given below, serve to explain the principles of the invention. As shown throughout the drawings, like reference numerals designate like or corresponding parts.

As employed herein, the statement that two or more parts or components are "coupled" together shall mean that the parts are joined or operate together either directly or through one or more intermediate parts or components.

As employed herein, the term "number" shall mean one or an integer greater than one (i.e., a plurality).

It has been hypothesized that asthma is the result of both a smooth muscle cell chemical deficiency (i.e., p38 MAPK and HSP27 inhibition) and a dynamic smooth muscle dilation deficiency (i.e., loss of mechanical perturbation and unencumbered muscle shortening resulting in excessive restriction of the airways). In plain English, this means that the upper airway in normal people is kept open because their upper airway smooth muscles can both process a key protein that is responsible for lengthening the muscle, and because they mechanically manipulate the airway muscles by more varied breathing patterns (i.e., a normal combination of both deep inspirations and more shallow inspirations). In asthmatic individuals, for some reason the processing of these key proteins is inhibited, which causes their airway muscles to be shorter (more constricted). Asthmatic individuals also do not have the same dynamic range of breathing, probably due to the shorter muscle state just described.

Positive pressure support systems that provide a flow of breathing gas to an airway of a patient at an elevated pressure are well known. One form of such pressure support is known as bi-level positive pressure support therapy. In bi-level positive pressure support therapy, the pressure of gas that is delivered to the patient varies with the patient's breathing cycle. Specifically, an inspiratory positive airway pressure (IPAP) is provided during the inspiratory phase of the patient's breathing cycle, and an expiratory positive airway pressure (EPAP) is provided during the expiratory phase of the patient's breathing cycle. The EPAP is lower than the IPAP so that the patient exhales against a relatively low pressure as compared to the IPAP pressure, thereby increasing the comfort to the patient. The BiPAP® and Bi-Flex® family of pressure support devices manufactured by Respironics, Inc. of Murrysville, Pa., are examples of pressure support devices that provide various forms of bi-level positive pressure support therapy. In addition, several U.S. patents describe bi-level positive pressure support system in detail, including U.S. Pat. Nos. 5,433,193; 5,313,937; 5,239,995; 5,148,802; 6,532,960; and 6,640,806, all of which are hereby expressly incorporated herein by reference as if set forth in their entirety herein.

Figure 1:
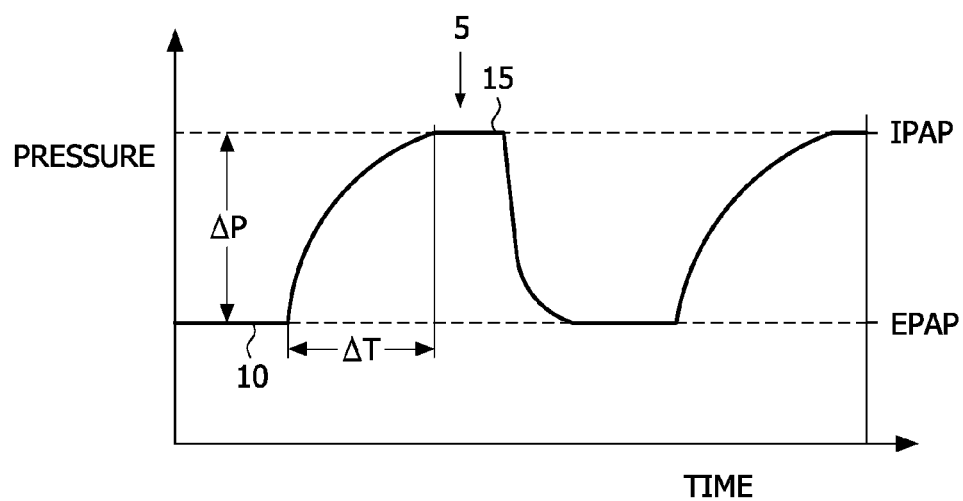
FIG. 1 is a typical prior art pressure curve that is output by a bi-level positive pressure support system.

As discussed above, a bi-level positive pressure support system (as that term is used herein) provides an IPAP level of pressure to the airway of a patient during at least a portion of inhalation and an EPAP level of pressure during at least a portion of exhalation. FIG. 1 schematically depicts a typical pressure curve 5 that is output by an exemplary bi-level positive pressure support system. During an expiratory phase of the patient's breathing cycle, the pressure curve 5 is at the expiratory pressure (EPAP) 10. At the end of exhalation, i.e., at the onset of the subsequent inhalation phase of the patient's breathing cycle, the pressure curve 5 changes to an inspiratory pressure (IPAP) 15. When the system detects the end of inspiration, i.e., at the onset of the subsequent exhalation phase, the pressure curve 5 returns to the lower expiratory pressure (EPAP) 10, and the cycle starts over. The difference in pressure between EPAP 10 and IPAP 15 is designated as ΔP in FIG. 1. As seen in FIG. 1, in the exemplary pressure waveforms shown therein, this pressure change occurs gradually (rather than instantaneously), which helps to improve patent comfort. This gradual transition effect is measured by the time it takes the system pressure to increase from EPAP 10 to IPAP 15 and is referred to as the "rise time" of the bi-level pressure support system. Similarly, rather than an instantaneous transition from IPAP 15 to EPAP 10, FIG. 1 shows a gradual transition of the system pressure from IPAP 15 to EPAP 10. This gradual transition effect is measured by the time it takes the system pressure to decrease from IPAP 15 to EPAP 10 and is referred to as the "fall time" of the bi-level pressure support system. Furthermore, while the transitions from EPAP 10 to IPAP 15 and from IPAP 15 to EPAP 10 are shown as exponential ramps in FIG. 1 (and in FIGS. 4, 6 and 7 described elsewhere herein), that is meant to be exemplary only and it should be understood that the ramping may also be a straight line (fixed rates of transition) or any other transitional waveform (including a square wave) from one generally constant level to another.

As described in greater detail herein, the present invention, in various embodiments, provides for the treatment of lung diseases that effect the airways, such as asthma and COPD, using positive pressure support therapy, preferably bi-level positive pressure support therapy. Specifically, the present invention employs positive pressure support therapy, preferably bi-level positive pressure support therapy, to address the upper airway muscle mechanical perturbation issues and deficiencies common to individuals suffering from lung diseases that effect the airways, such as asthmatic individuals. More specifically, in one embodiment, the present invention treats lung disease, such as asthma or COPD, using positive pressure support therapy, preferably bi-level positive pressure support therapy, by determining a parameter indicative of the patient's pulmonary mechanics, such as, without limitation, upper airway resistance or lung compliance, and then determining and varying the positive pressure support therapy settings (e.g., the pressure level during at least a portion of the inspiratory phase or the IPAP and EPAP settings) based on the determined parameter. In another embodiment, the present invention treats lung disease, such as asthma or COPD, using positive pressure support therapy, preferably bi-level positive pressure support therapy, by dynamically and preferably pseudo-randomly varying the positive pressure support therapy settings (such as the pressure level during at least a portion of the inspiratory phase or the range of the IPAP and EPAP settings) employed during the positive pressure support therapy session. The positive pressure support therapy methods described herein are preferably intended to be used by an individual regularly, such as, without limitation, one or more times each day, to treat the individual's condition, regardless of whether the individual is currently suffering any acute symptoms. One goal or objective of the therapy is to diminish the individual's need for controller and/or rescue medications.

Figure 2:
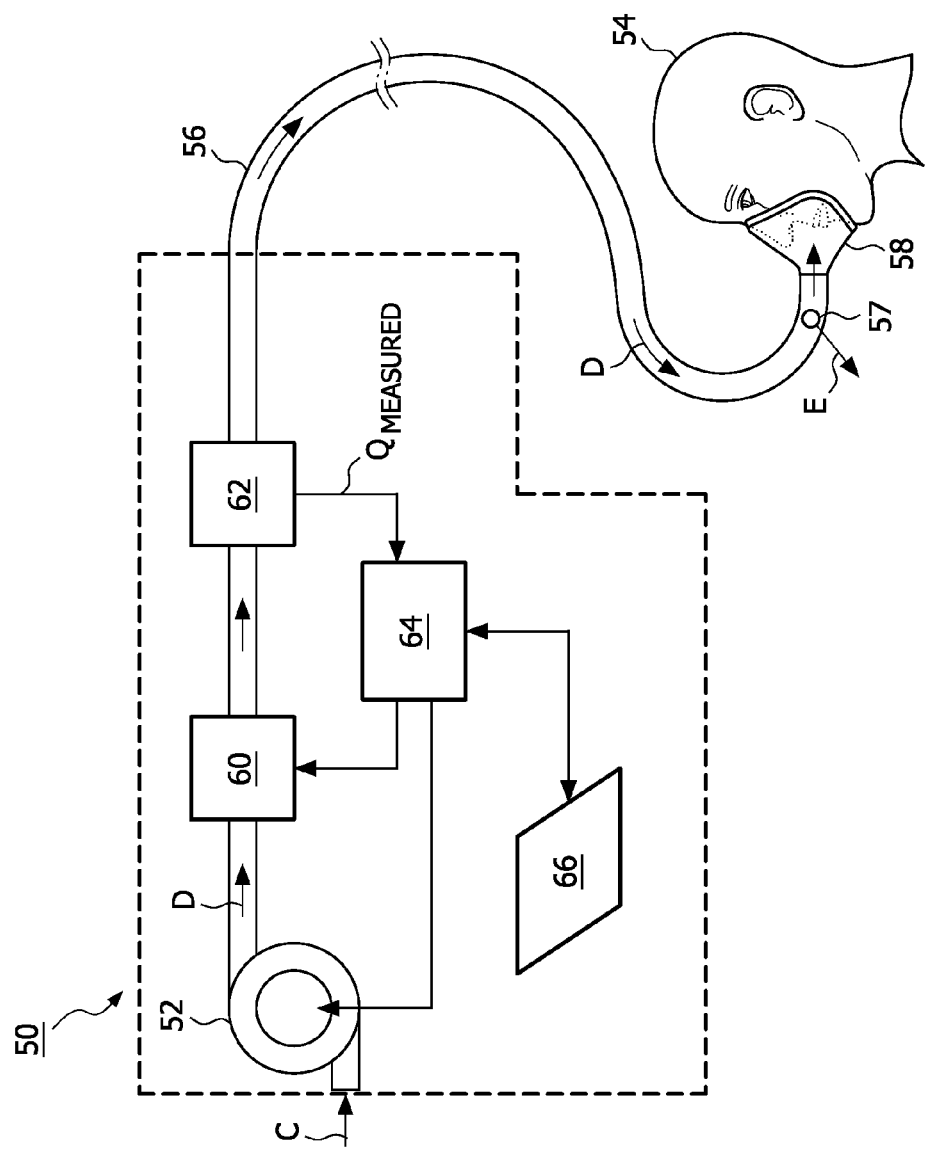
FIG. 2 is a pressure support system according to one, non-limiting embodiment of the invention.

As noted above, in the preferred embodiments, the positive pressure support that is provided to the patient is bi-level positive pressure support. Thus, for ease of illustration and explanation, the particular embodiments described below (FIGS. 2 through 7) will employ such bi-level positive pressure support. It is to be understood, however, that that is not meant to be limiting, and that other forms of positive pressure support (i.e., other therapeutic waveforms where the pressure delivered to the user is above atmospheric pressure) provided during at least part of the inspiratory phase and possibly also during the at least part of the expiratory phase of the patient are also contemplated. FIG. 2 is a schematic diagram of a pressure support system 50 according to one particular, non-limiting embodiment that may be adapted to provide bi-level positive pressure support therapy for treating lung disease, such as asthma or COPD, as described herein. Referring to FIG. 2, the pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. The gas flow generator 52 generates a flow of breathing gas, such as air, oxygen, or a mixture thereof, for delivery to an airway of a patient 54 at relatively higher and lower pressures, i.e., generally equal to or above ambient atmospheric pressure. The pressurized flow of breathing gas, generally indicated by arrow D from the gas flow generator 52, is delivered via a delivery conduit 56 to a breathing mask or patient interface 58 of any known construction, which is typically worn by or otherwise attached to the patient 54 during therapy to communicate the flow of breathing gas to the airway of the patient. The delivery conduit 56 and the patient interface device 58 are typically collectively referred to as a patient circuit.

The pressure support system 50 shown in FIG. 2 is what is known as a single-limb system, meaning that the patient circuit includes only a delivery conduit 56 connecting the patient 54 to the pressure support system 50. As such, an exhaust vent 57 is provided in the delivery conduit 56 for venting exhaled gasses from the system as indicated by arrow E. It should be noted that the exhaust vent 57 can be provided at other locations in addition to or instead of in the delivery conduit 56, such as in the patient interface device 58. It should also be understood that the exhaust vent 57 can have a wide variety of configurations depending on the desired manner in which gas is to be vented from the pressure support system 50.

The present invention also contemplates that the pressure support system 50 can be a two-limb system, having a delivery conduit and an exhaust conduit connected to the patient 54. In a two-limb system, the exhaust conduit carries exhaust gas from the patient 54 and includes an exhaust valve at the end distal from the patient 54. The exhaust valve in such an embodiment is typically actively controlled to maintain a desired level or pressure in the system, which is commonly known as positive end expiratory pressure (PEEP).

Furthermore, in the illustrated exemplary embodiment of the pressure support system 50 shown in FIG. 2, the patient interface 58 is a full face mask. It is to be understood, however, that the patient interface 58 can include a nasal/oral mask, nasal pillows, or any other device that provides a suitable gas flow communicating function. Also, for purposes of the present invention, the phrase "patient interface" can include the delivery conduit 56 and any other structures that connect the source of pressurized breathing gas to the patient.

In the illustrated embodiment, the pressure support system 50 includes a pressure controller in the form of a valve 60 provided in the delivery conduit 56. The valve 60 controls the pressure of the flow of breathing gas from the flow generator 52 that is delivered to the patient 54. For present purposes, the flow generator 52 and the valve 60 are collectively referred to as a pressure generating system because they act in concert to control the pressure and/or flow of gas delivered to the patient. However, it should be apparent that other techniques for controlling the pressure of the gas delivered to the patient, such as varying the blower speed of the flow generator 52, either alone or in combination with a pressure control valve, are contemplated by the present invention. Thus, the valve 60 is optional depending on the technique used to control the pressure of the flow of breathing gas delivered to the patient 54. If the valve 60 is eliminated, the pressure generating system corresponds to the flow generator 52 alone, and the pressure of gas in the patient circuit is controlled, for example, by controlling the motor speed of the flow generator 52.

The pressure support system 50 further includes a flow sensor 62 that measures the flow of the breathing gas within the delivery conduit 56. In the particular embodiment shown in FIG. 2, the flow sensor 62 is interposed in line with the delivery conduit 56, most preferably downstream of the valve 60. The flow sensor 62 generates a flow signal $Q_{MEASURED}$ that is provided to a controller 64 and is used by the controller 64 to determine the flow of gas at the patient 54. Of course, other techniques for measuring the respiratory flow of the patient 54 are contemplated by the present invention, such as, without limitation, measuring the flow directly at the patient 54 or at other locations along the delivery conduit 56, measuring patient flow based on the operation of the flow generator 52, and measuring patient flow using a flow sensor upstream of the valve 60. The controller 64 may be, for example, a microprocessor, a microcontroller or some other suitable processing device, that includes or is operatively coupled to a memory (not shown) that provides a storage medium for data and software executable by the controller 64 for controlling the operation of the pressure support system 50, including monitoring characteristics of patient respiration and controlling the flow of breathing gas based thereon as described in greater detail herein. Finally, an input/output device 66 is provided for setting various parameters used by the pressure support system 50, as well as for displaying and outputting information and data to a user, such as a clinician or caregiver.

Figure 3A:
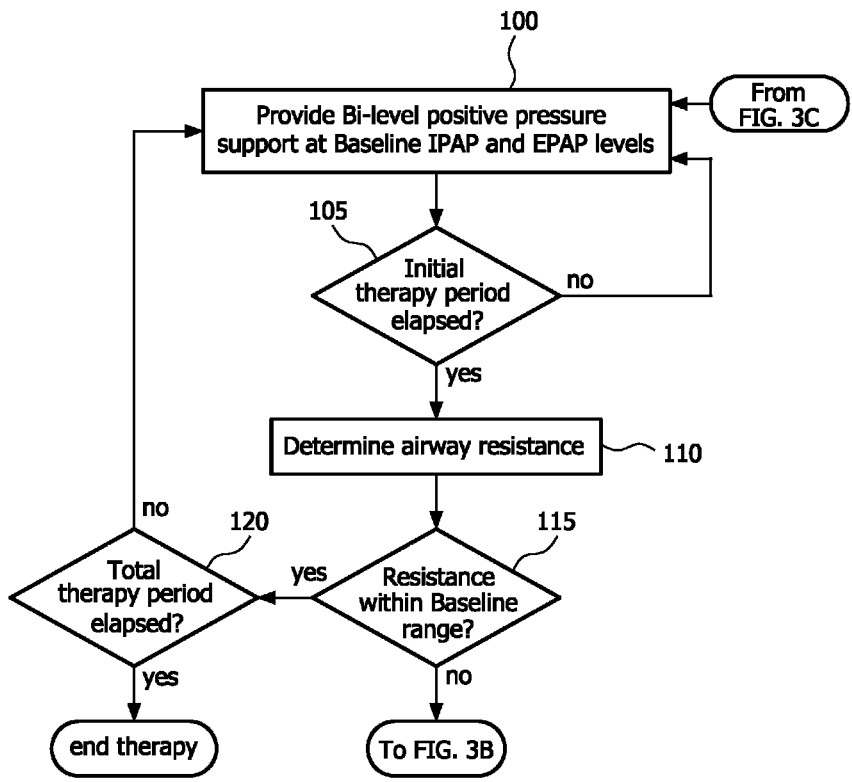
FIGS. 3A, 3B and 3C are a flowchart showing a method of treating asthma according to one particular, non-limiting embodiment of the invention using bi-level positive pressure support therapy.
Figure 3B:
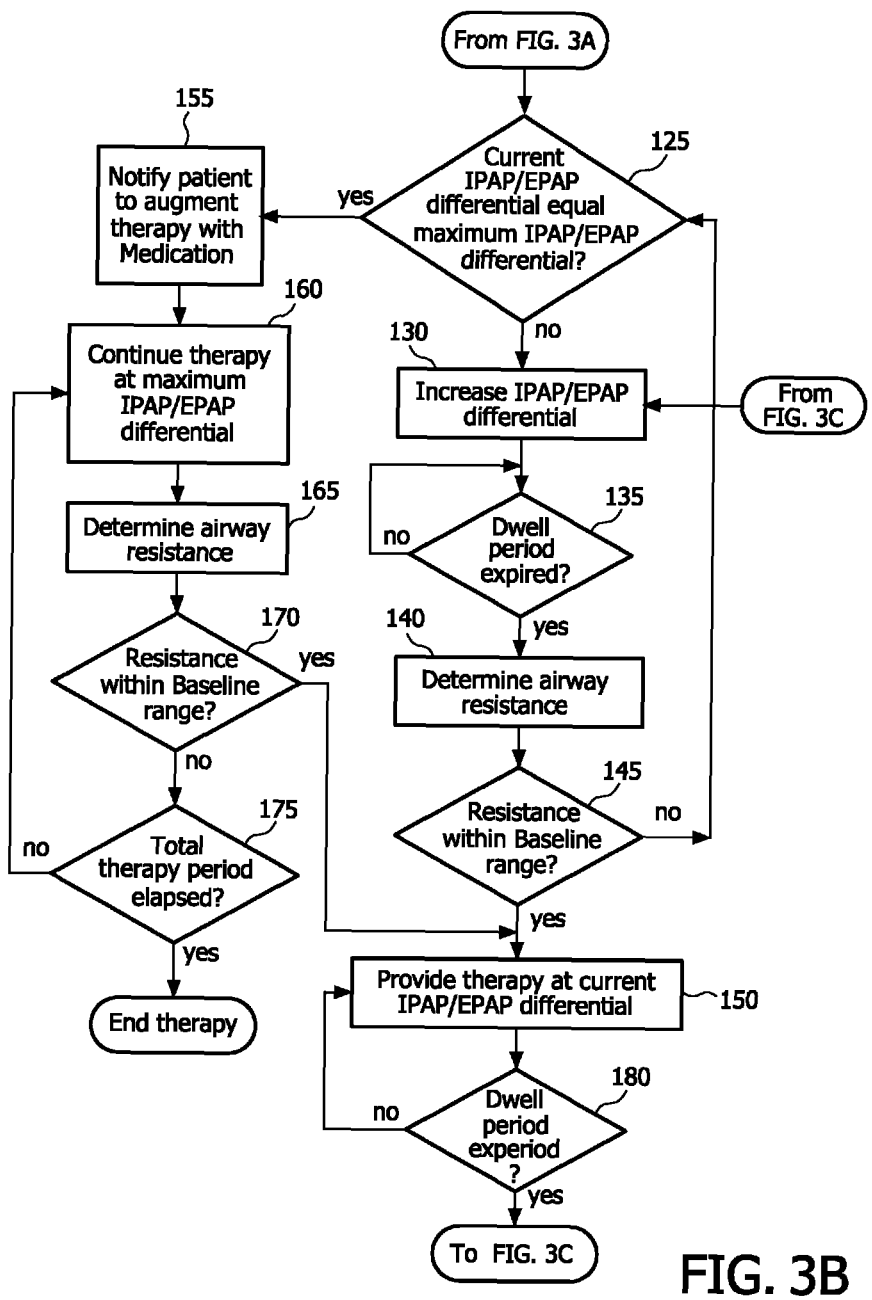
Figure 3C:
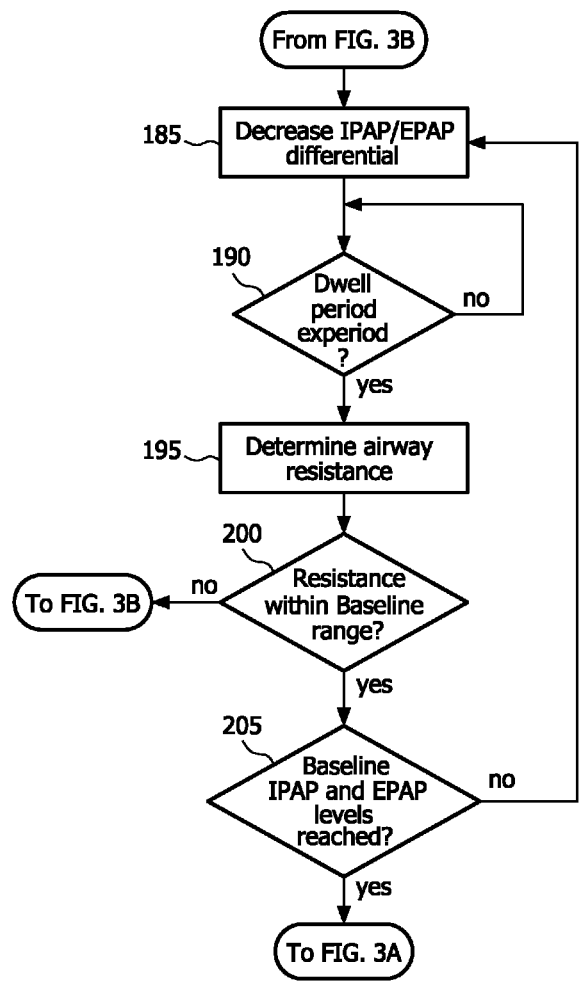

FIGS. 3A, 3B and 3C are a flowchart showing a method of treating lung disease, such as asthma or COPD, according to one particular, non-limiting embodiment of the invention using bi-level positive pressure support therapy. The method shown in FIGS. 3A, 3B and 3C may be implemented in the exemplary pressure support system 50 shown in FIG. 2 (or in another suitable pressure support system). For illustrative purposes, the method will be described herein as implemented in the pressure support system 50. In the method shown in FIGS. 3A, 3B and 3C, lung disease, such as asthma or COPD, therapy is provided by determining a parameter indicative of the patient's pulmonary mechanics, and then determining and varying the bi-level positive pressure support therapy settings (e.g., without limitation, the IPAP/EPAP differential ΔP) based on the determined parameter. In the particular embodiment shown in FIGS. 3A, 3B and 3C, the parameter indicative of the patient's pulmonary mechanics that is used is the patient's upper airway resistance. It is to be understood that that is merely the preferred parameter that may be used, and is not meant to be limiting. Other suitable parameters that may be determined by the pressure support system 50 such as, without limitation, lung compliance, may also be employed.

A number of different suitable methods for determining upper airway resistance and/or lung compliance using the pressure support system 50 are possible. Such methods include methods based on a measured flow signal (e.g., $Q_{MEASURED}$ in FIG. 2). However, as is known, one of the most challenging problems in the non-invasive estimation of upper airway resistance and/or lung compliance relates to how to eliminate the effects of the diaphragmatic muscle pressure ($P_{mus}$) on the measured flow signal, since the $P_{mus}$ component in the flow signal typically leads to large estimation errors.

The assignee of the present invention has developed a flow signal-based method for the non-invasive estimation of upper airway resistance and/or lung compliance that is based on the single compartment lung model and that resolves the issue of the $P_{mus}$ component using bi-level therapy. Specifically, two different IPAP pressures (e.g., 2 cmH$_2$O apart) are applied on successive breaths, and the flow responses are measured and then subtracted from one another. Subtracting the flow responses removes the flow component caused by the diaphragm (i.e., the $P_{mus}$ component), leaving a signal that is the result of the pressure difference applied by the external source. A least squares error fit of the data may then be used to determine the upper airway resistance and lung compliance. Specifically, using least squares linear regression analysis of the natural logarithm of the exponential flow response of a single compartment model to the external pressure source, intercept and slope can be determined. From these values, the time constant and lung compliance can be determined, which then allows the upper airway resistance to be determined.

The assignee of the present invention has also developed a similar, yet slightly different, method for estimating lung compliance and airway resistance by using the first-order single-compartment lung model equations and a randomized pattern of varying the pressure support (pressure support is the difference between the pressure applied during inspiration and expiration). This alternate method resolves the issue of the $P_{mus}$ component by taking the difference of the volume response of the system for two different inspiratory pressure settings on successive breaths. With this technique, the lung compliance and $P_{mus}$ can be simply estimated using the steady-state response of the differential volume signal, or approximating this steady state value through numerical methods. An estimation of the airway resistance can follow by using the time response information in the differential volume signal and compliance estimate.

While the particular methods for determining lung compliance and/or airway resistance just described are believed to be particularly applicable to the invention as described herein, a number of other methods for determining upper airway resistance and/or lung compliance are known in the art and may also be utilized in the present invention. For example, United States Patent Application Publication No. 2004/097821, entitled "Method and Breathing Apparatus for Assessing Pulmonary Stress," describes a method for determining lung resistance and compliance that utilizes a single compartment model. In particular, an equation that relates pressure and flow of the single compartment model is directly used to determine resistance and compliance. These values are then used to determine a stress index value that represents the pulmonary stress existing in the respiratory system. U.S. Pat. No. 6,257,234, entitled "Apparatus and Method for Determining Respiratory Mechanics of a Patient and for Controlling a Ventilator Based Thereon", describes a method for non-invasively detecting the resistance and elastance of the patient's respiratory system using forced single pressure oscillation in a range of 3-10 Hz and 2-10 cmH2O. Resistance is detected by controlling the ventilator to superimpose at least one forced single pressure oscillation on the therapeutic pressure and then observing the pressure-flow relation. Elastance is detected by controlling the ventilator to supply a pressure which has the affect of temporarily occluding the respiratory system, waiting until the respiratory system has reached equilibrium, and evaluating the pressure-volume relation. The resistance and elastance parameters are calculated using two or more data points from the pressure, flow and volume signals. U.S. Pat. No. 5,881,724, entitled "Method and Device for Controlling a Respirator for Therapeutic Treatment of Sleep Apnea", describes a method where an individual's respiratory resistance is determined based on the measured pressure amplitude by oscilloresistometry. Specifically, sine wave flow is superimposed onto the respiratory flow and the resultant pressure oscillation is used to determine resistance. U.S. Pat. No. 6,837,242, entitled "Method and Apparatus for Determining Respiratory System Resistance During Assisted Ventilation", describes a method wherein resistance is calculated using a known value of compliance and a measured pressure, volume and flow. Specifically, resistance is measured by finding the pressure-flow relationship through the introduction of perturbations in pressure, flow and volume. $P_{max}$ is estimated using the total pressure, volume and flow.

Referring to FIGS. 3A, 3B and 3C, the method shown therein will now be described. As described in greater detail below, that method assumes that a baseline upper airway resistance range which represents a normal, non-diseased (e.g., non-asthmatic) condition, has been established. That baseline resistance range may be, for example, preset by a clinician or established by the pressure support system 50 by taking a number of resistance measurements during a time when the patient is not suffering from disease (e.g., asthmatic) symptoms. In addition, the method shown in FIGS. 3A, 3B and 3C also assumes that a baseline level of bi-level positive pressure support at baseline IPAP and EPAP levels has been established, preferably by being input into the pressure support system 50 by a clinician. Thus, the baseline bi-level positive pressure support will have a baseline IPAP/EPAP differential, ΔP, as shown, for example, in FIG. 1. As described in greater detail below, the actual bi-level positive pressure support that is provided to the patient during therapy according to the present method will be varied around and as compared to this baseline therapy based upon the particular airway resistance measurements that are made.

Referring to FIG. 3A, the method begins at step 100, wherein the patient 54 attaches the patient interface 58 in the required manner and bi-level positive pressure support at the baseline IPAP and EPAP levels is provided by the pressure support system 50. The particular embodiment of the method shown in FIGS. 3A, 3B and 3C will provide this baseline level of support for an initial therapy period before the resistance measurements are made and the level of support is varied. Thus, at step 105, a determination is made as to whether the initial therapy period has elapsed. Such initial therapy period may be, for example, five to ten minutes. If the answer at step 105 is no, the method returns to step 100. If, however, the answer at step 105 is yes, meaning that the initial therapy period has elapsed, then, at step 110, the pressure support system 50 determines the airway resistance of the patient 54 using, for example and without limitation, one of the methods described elsewhere herein. Next, at step 115, a determination is made as to whether the measured airway resistance is within the pre-established baseline range. If the answer is yes, then, at step 120, a determination is made as to whether a preset total therapy period has elapsed. That preset total therapy period is the total period over which the therapy of the present invention is to be provided in the current therapy session. If the answer at step 120 is yes, then the therapy is ended and the bi-level positive pressure support is no longer provided by the pressure support system 50. If, however, the answer at step 120 is no, then the method returns to step 100.

As seen in FIG. 3A, if the answer at step 115 is no, meaning that the determined airway resistance is not within the pre-established normal baseline range, then the method proceeds to step 125 shown in FIG. 3B. As described in greater detail below, the method embodiment shown in FIGS. 3A, 3B and 3C is able to increase the IPAP/EPAP differential up to some preset maximum level. Thus, at step 125, a determination is made as to whether the current IPAP/EPAP differential is equal to the preset maximum IPAP/EPAP differential (i.e., has the maximum IPAP/EPAP differential been reached). If the answer at step 125 is no, then, at step 130, the IPAP/EPAP differential is increased by a predetermined amount. For example, this may be done by both increasing the IPAP level and decreasing the EPAP level, by only increasing the IPAP level or by only decreasing the EPAP level. The amount of the increase is a predetermined step amount that is preferably set by a clinician using the input/output device 66 of the pressure support system 50. In the embodiment shown in FIGS. 3A, 3B and 3C, each time the IPAP/EPAP differential is increased, the therapy will be allowed to dwell for a predetermined dwell period. That predetermined dwell period may be, for example and without limitation, one or more breathing cycles of the patient. Thus, at step 135, a determination is made as to whether the predetermined dwell period has expired. If the answer is no, then the method returns to step 135. If, however, the answer is yes, then, at step 140, the airway resistance is again determined, preferably according to one of the methods described herein. Next, at step 145, a determination is made as to whether the determined airway resistance is within the predetermined baseline range. If the answer at step 145 is no, then, the method returns to step 125. If, however, the answer at step 145 is yes, then the method proceeds to step 150, which is described in greater detail below.

Referring again to step 125, if the answer is yes, meaning that the current IPAP/EPAP differential equals the maximum IPAP/EPAP differential, the method proceeds to step 155. At step 155, the patient is notified to augment the therapy being provided with their medication (e.g., asthma medication). For example, the patient 54 may temporarily remove the patient interface 58 and administer a rescue medication. After the medication is delivered, the patient 54 reattaches the patient interface 58. Alternatively, a medication delivery device such as a nebulizer may be coupled to the patient interface 58 as described in, for example and without limitation, U.S. Pat. No. 5,297,543, entitled "Medication Inhaler Mixer", and United States Patent Application Publication No. 2006/0201500, entitled "Nebulizer Drug Delivery Device for Ventilator", both owned by the assignee hereof, the disclosures of which are incorporated herein by reference. In such an embodiment, at step 155, the pressure support system 50 will automatically cause the medication delivery device to deliver a medication to the patient 54 as therapy is continued. Next, following step 155 (regardless of implementation), the method proceeds to step 160, wherein bi-level positive pressure support therapy at the maximum IPAP/EPAP differential is continued for a predetermined period of time. Thereafter, at step 165, the airway resistance is again determined. Then, at step 170, a determination is made as to whether the determined resistance is within the predetermined baseline range. If the answer is no, then, at step 175, a determination is made as to whether the total therapy period has elapsed. If the answer is yes, then therapy is ended. If, however, the answer is no, then the method returns to step 160. If, however, the answer at step 170 is yes, meaning that the determined airway resistance is within the baseline range, then the method proceeds to step 150.

At step 150, which may be reached as a result of either a positive answer at step 145 or a positive answer at step 170 (both meaning that the current determined resistance is within the baseline range), the bi-level positive pressure support therapy is provided at the then current IPAP/EPAP differential. Furthermore, that level of therapy will be provided for a predetermined dwell period. Thus, at step 180, a determination is made as to whether the dwell period has expired. If the answer is no, then the method returns to step 150, wherein therapy is continued. If, however, the answer at step 180 is yes, meaning that the dwell period has expired, then the method proceeds to step 185 in FIG. 3C.

At step 185, the IPAP/EPAP differential is decreased by a predetermined step amount. This step is, in effect, the opposite of step 130 and will preferably be performed in an opposite manner, meaning that depending on the particular implementation used for the increase (described above) the IPAP level may be decreased and the EPAP level may be increased, only the IPAP may be decreased, or only the EPAP level may be increased, in order to achieve the predetermined step decrease. Next, at step 190, a determination is made as to whether the predetermined dwell period has expired. If the answer is no, then the method returns to step 190 in effect creating a loop that awaits the expiration of the dwell period. If, however, the answer at step 190 is yes, meaning that the dwell period has expired, then, at step 195, the airway resistance of the patient 54 is determined as described elsewhere herein. At step 200, a determination is made as to whether the resistance that is determined is within the predetermined baseline range. If the answer at step 200 is no, then the method returns to step 130 of FIG. 3B and the IPAP/EPAP differential is increased as described previously. If, however, the answer at step 200 is yes, then, at step 205, a determination is made as to whether the baseline IPAP and EPAP levels have been reached. If the answer at step 205 is no, then the method returns to step 185, and the IPAP/EPAP differential is further decreased by a predetermined step as described. If the answer at step 205 is yes, meaning that the baseline level of therapy has been reached, then the method returns to step 100 of FIG. 3A and processing continues as described previously.

Thus, in short, according to an aspect of the present invention, and as shown in the particular exemplary embodiment of FIGS. 3A, 3B and 3C, as airway resistance measurements indicate an increase in airway resistance as compared to a baseline (which increase indicates a worsening of the systems of the patient 54), the IPAP/EPAP differential will be increased at predetermined increments or magnitudes. The IPAP/EPAP differential will continue to be increased until the airway resistance of the patient improves, or until the predetermined maximum IPAP/EPAP differential is reached. If the maximum IPAP/EPAP differential is reached without the desired improvement in the airway resistance of the patient 54, then the patient 54 is notified to augment the bi-level positive pressure support therapy with their medication (e.g., asthma medication) (alternatively, the medication may be administered automatically as described herein by an integrated delivery device). If the airway resistance of the patient 54 is able to be improved with the increased IPAP/EPAP differential, then the therapy will dwell at that setting for a predetermined duration of time, and thereafter the IPAP/EPAP differential will be decreased in a step-wise fashion. If the airway resistance of the patient remains normal as the IPAP/EPAP differential is decreased, it will be decreased until the baseline level is reached. Otherwise, if during the IPAP/EPAP differential reduction the airway resistance moves away from normal, then the IPAP/EPAP differential is again increased in effort to reestablish the normal airway resistance.

Figure 4:
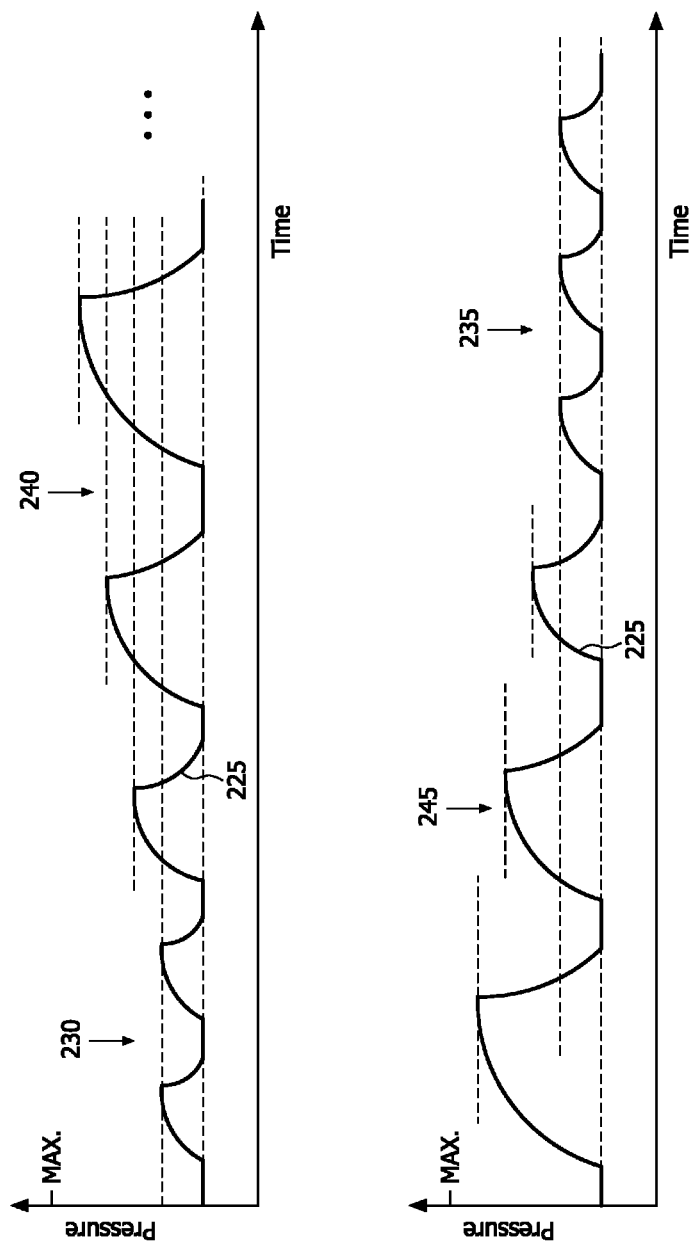
FIG. 4 is an exemplary pressure curve that may result from the method of FIGS. 3A, 3B and 3C.

FIG. 4 shows an exemplary pressure curve 225 that may provide bi-level positive pressure support therapy to the patient 54 according to the method shown in FIGS. 3A, 3B and 3C. As seen in FIG. 4, the pressure curve 225 includes sections 230 and 235 where the baseline bi-level positive pressure support therapy is provided, a section 240 wherein the IPAP/EPAP differential is increased, and a section 245 wherein the IPAP/EPAP differential is decreased. For illustrative purposes, sections of the pressure curve 225 that may include variations resulting from one or more methods of determining airway resistance are omitted. Furthermore, it will be appreciated that the pressure curve 225 is but one exemplary possibility that may result from the method shown in FIGS. 3A, 3B and 3C, and that many other variations are possible.

Furthermore, in the particular embodiment shown in FIGS. 3A, 3B and 3C, the parameter indicative of the patient's pulmonary mechanics that is employed is upper airway resistance. It should be understood, however, that that is not meant to be limiting, and that instead other such parameters, including, without limitation, lung compliance, may also be employed without departing from the scope of the present invention.

In addition, in the particular embodiment shown in FIGS. 3A, 3B and 3C, the parameter indicative of the patient's pulmonary mechanics is determined in a separate step from the resulting therapy (which preferably has a fixed duration). This, however, does not have to be the case. Instead, the parameter indicative of the patient's pulmonary mechanics (e.g., resistance or lung compliance) can be determined during therapy, and the pressures can be modified/titrated simultaneously, in real time.

Furthermore, in the particular embodiment shown in FIGS. 2, 3A, 3B and 3C, the parameter indicative of the patient's pulmonary mechanics is determined by the pressure support system 50. This is merely one particular embodiment. Alternately, the determination of the parameter indicative of the patient's pulmonary mechanics could be accomplished by a separate (external to the pressure support system 50) device and transmitted, wired or wirelessly, to the pressure support system 50. For example, a hand-held (portable) spirometer, which is a device used by asthma patients to determine effectiveness of therapy, could be employed to determine the parameter indicative of the patient's pulmonary mechanics and automatically transmit the determined data to the pressure support system 50 through an appropriate interface provided as a part thereof for use in the methods as described elsewhere herein. As a further alternative, the data determined by the separate device such as a spirometer can be manually input (as opposed to automatically transmitted) into the pressure support system 50 using a suitable user interface such as a keypad or touchscreen for use in the methods as described elsewhere herein.

In still another particular embodiment, a device like a modem, memory card, or other data connectivity method, could be used to send data to the patient's care provider relating to compliance and effectiveness of therapy for a predetermined time period (e.g., respiratory resistance or lung compliance over one or more days). In addition, in another particular embodiment, the pressure support system 50 can have a feedback component that indicates to the user how well they are stretching their lungs. For example, an "effectiveness of therapy" feedback component could be displayed numerically and/or graphically on a display provided as part of the pressure support system 50, and/or provided in the form of auditory feedback using a feedback device such as a speaker provided as part of the pressure support system 50. One method of feedback could indicate increasing (or decreasing) tidal volume of the user resulting from the therapy over a predetermined period of time, or meeting or exceeding a target tidal volume. As known in the art, tidal volume can be determined by integrating airflow through portions of the respiratory cycle.

Figure 5:
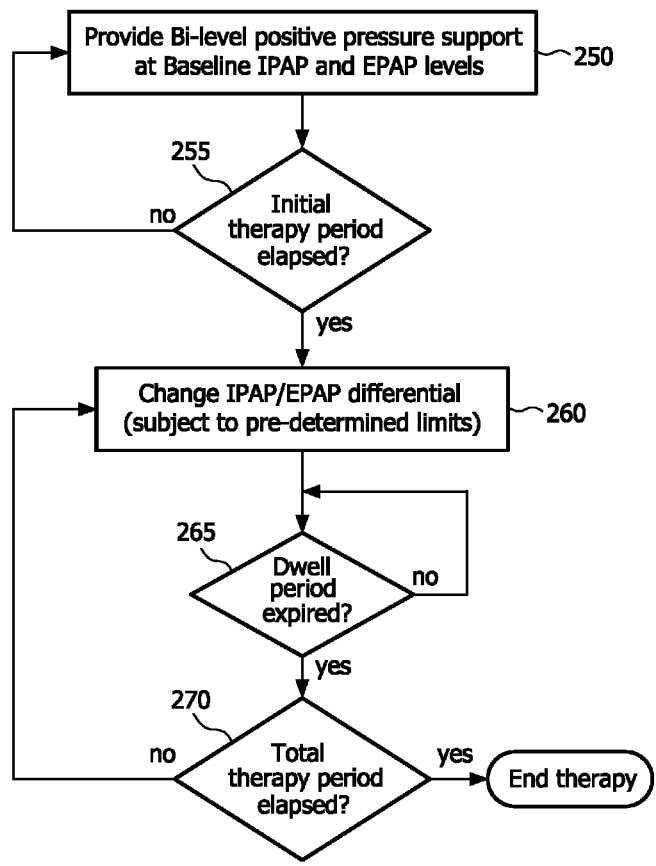
FIG. 5 is a flowchart showing a method of treating asthma according to an alternative embodiment of the invention using bi-level positive pressure support therapy.

FIG. 5 is a flowchart showing a method of treating asthma according to an alternative embodiment of the invention using bi-level positive pressure support therapy. The method of FIG. 5 may be implemented in the exemplary pressure support system 50 shown in FIG. 2 (or in another suitable pressure support system). In the method shown in FIG. 5, asthma therapy is provided by periodically changing the IPAP/EPAP differential that is provided to the patient 54 as compared to a baseline level. In other words, the range of the IPAP and EPAP settings are, in this embodiment, varied to dynamically manipulate the muscles of the patient's upper airway. Preferably, the particular IPAP and EPAP settings, (i.e., the particular IPAP/EPAP differentials), are determined and set pseudorandomly. Alternatively, the particular IPAP and EPAP settings may be varied according to some predetermined scheme (e.g., a preset pattern) that provides a suitable dynamic manipulation of the muscles of the patient's upper airway.

Referring to FIG. 5, the method begins at step 250, wherein bi-level positive pressure support is provided to the patient 54 by the pressure support system 50 at a predetermined baseline level (i.e., at predetermined baseline IPAP and EPAP levels). Preferably, that baseline level is established by a clinician using the input/output device 66 of the pressure support system 50. In the embodiment shown in FIG. 5, that baseline bi-level positive pressure support therapy is provided for a predetermined initial therapy period which also is preferably established by a clinician using the input/output device 66 of the pressure support system 50. Thus, at step 255, a determination is made as to whether that initial therapy period has elapsed. If the answer is no, then the method returns to step 250, and baseline therapy is continued. If, however, the answer at step 255 is yes, then, at step 260, the IPAP/EPAP differential is changed, either pseudorandomly (within certain predetermined safe limit values) or according to a predetermined scheme that is stored by the controller 64. In the embodiment shown in FIG. 5, the new bi-level positive pressure support therapy at the new IPAP/EPAP differential is provided for a particular dwell period. Thus, following step 260, the method proceeds to step 265, wherein a determination is made as to whether the dwell period has expired. If the answer at step 265 is no, then the method returns to step 265. If, however, the answer at step 265 is yes, meaning that the dwell period has expired, then the method proceeds to step 270, wherein a determination is made as to whether a predetermined total therapy period has elapsed. Preferably, that predetermined total therapy period, which indicates the total time for which the therapy of FIG. 5 is to be provided, is established by a clinician and/or the patient 54 using the input/output device 66 of the pressure support system 50. If the answer at step 270 is no, meaning that therapy is to continue, then the method returns to step 260, where the IPAP/EPAP differential is again changed. If the answer at step 270 is yes, meaning that the total therapy period has elapsed, then therapy ends. Thus, the method of FIG. 5 will, following an initial period of baseline therapy, result in bi-level positive pressure support therapy with periodically varying IPAP and EPAP settings being provided to the patient 54 until a predetermined therapy period has elapsed.

The dwell period of step 265 may, for example, be equal to the length of one breathing cycle of the patient 54, in which case the IPAP/EPAP differential will change breath-to-breath, or, alternatively, may encompass multiple breathing cycles of the patient 54, in which case the IPAP/EPAP differential will remain the same for a number of breathing cycles and then change to a new level for a number of breathing cycles, and so on.

Figure 6:
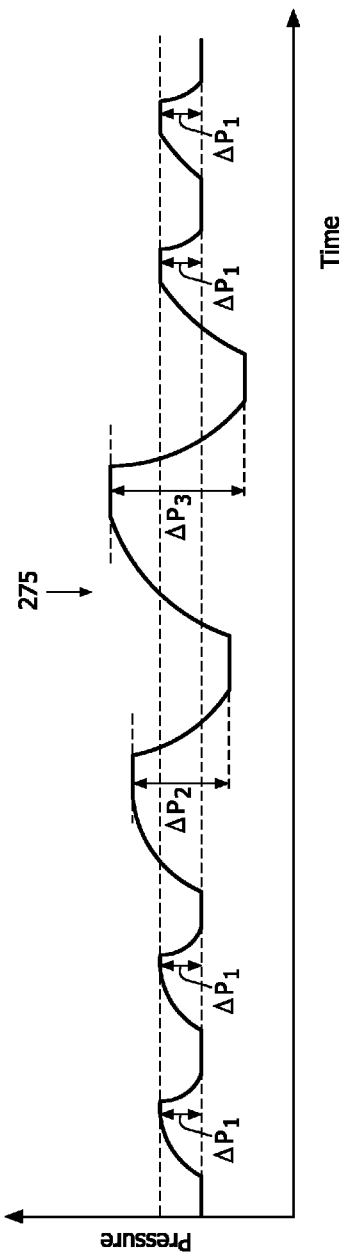
FIGS. 6 and 7 show exemplary pressure curves that may result from the method of FIG. 5.
Figure 7:
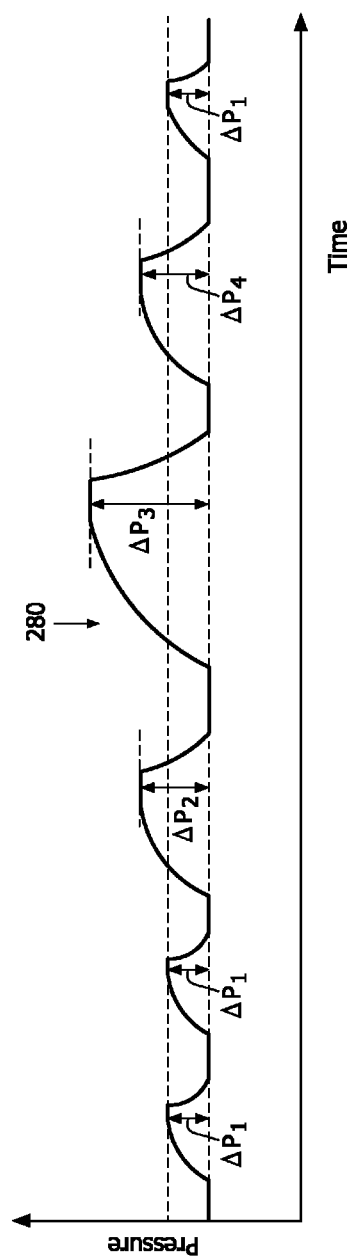

FIGS. 6 and 7 show exemplary pressure curves 275 and 280, respectively, which may result from the method shown in FIG. 5. As seen in FIGS. 6 and 7, the pressure curves 275 and 280 include baseline IPAP/EPAP differentials, indicated by $\Delta P_1$, and varying IPAP/EPAP differentials, indicated by $\Delta P_2$, $\Delta P_3$ and, in the case of pressure curve 280, $\Delta P_4$. Again, the pressure curves 275 and 280 shown in FIGS. 6 and 7, respectively, are meant to be exemplary only and are not meant to be limiting. Thus, other pressure curves having IPAP/EPAP differentials that vary in other ways may also result from the method shown in FIG. 5 and thus are within the scope of the present invention.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. For example, the embodiments disclosed elsewhere herein have been described in connection with the treatment of asthma. However, the methods and system described herein may be employed to treat other lung diseases that effect the airways, such as, without limitation, chronic obstructive pulmonary disease (COPD). Accordingly, the invention is not to be considered as limited by the foregoing description but is only limited by the scope of the appended claims.

What is claimed is:

1. A method of treating lung disease in a patient, comprising:
   determining, with a controller, a parameter indicative of the patient's pulmonary mechanics, the parameter determination comprising:
   (1) measuring, with one or more sensors, flow responses produced by two different parameter determination inspiratory positive airway pressure (IPAP) levels delivered to the patient during two successive breaths, subtracting the flow responses from one another, and performing a least squares error fit on flow data that results from the subtraction; or
   (2) randomly varying a level of parameter determination pressure support delivered to the patient during the two successive breaths, determining a differential volume signal by subtracting volume responses measured during the two successive breaths from one another, and estimating a steady-state response of the differential volume signal;
   generating, with a pressure support system, therapy positive pressure support for delivery to an airway of the patient, wherein a pressure level of the therapy positive pressure support during at least a portion of an inspiratory phase of the patient is determined based on the determined parameter, wherein the pressure level of the therapy positive pressure support during at least a portion of the inspiratory phase includes a peak pressure, and determining a second pressure level that is below the peak pressure of the therapy positive pressure support, the second pressure level being determined during an expiratory phase of the patient, the second pressure level determined based on the determined parameter.

2. The method according to claim 1, wherein generating the therapy positive pressure support for delivery to an airway of the patient comprises delivering bi-level positive pressure support to an airway of the patient, the bi-level positive pressure support having an IPAP level and an expiratory positive airway pressure (EPAP) level, wherein the IPAP level and the EPAP level of the bi-level positive pressure support are determined based on the determined parameter.

3. The method according to claim 1, wherein the determining a parameter step is performed prior to the generating therapy positive pressure support step.

4. The method according to claim 1, wherein the lung disease is asthma.

5. The method according to claim 1, wherein the lung disease is COPD.

6. The method according to claim 1, wherein the parameter is upper airway resistance.

7. The method according to claim 1, wherein the parameter is lung compliance.

8. The method according to claim 1, wherein the generating is performed by the pressure support system and wherein the determining the parameter indicative of the patient's pulmonary mechanics comprises determining the parameter with a device external to the pressure support system and providing the parameter to the pressure support system.

9. The method according to claim 1, wherein the generating is performed by the pressure support system and wherein the determining the parameter indicative of the patient's pulmonary mechanics comprises determining the parameter external to the pressure support system and manually inputting the parameter into the pressure support system.

10. The method according to claim 1, further comprising repeating the method one or more times a day regardless of whether the patient is suffering acute symptoms of lung disease to reduce the patient's reliance on medication.

11. A pressure support system for treating lung disease, comprising:
a pressure generating system adapted to produce a flow of breathing gas;
a patient circuit operatively coupled to the pressure generating system to deliver the flow of breathing gas to an airway of a patient; and
a controller operatively coupled to the pressure generating system, the controller being adapted to:
  determine a parameter indicative of the patient's pulmonary mechanics, the parameter determination comprising:
    (1) measuring, with one or more sensors, flow responses produced by two different parameter determination inspiratory positive airway pressure (IPAP) levels delivered to the patient during two successive breaths, subtracting the flow responses from one another, and performing a least squares error fit on flow data that results from the subtraction; or
    (2) randomly varying a level of parameter determination pressure support delivered to the patient during the two successive breaths, determining a differential volume signal by subtracting volume responses measured during the two successive breaths from one another, and estimating a steady-state response of the differential volume signal; and
  control the pressure generating system to deliver the flow of breathing gas to the patient at a therapy pressure level during at least a portion of an inspiratory phase of the patient, wherein the therapy pressure level is determined based on the determined parameter,
  wherein the therapy pressure level of the flow of breathing gas during the portion of the inspiratory phase includes a peak pressure, and
  the controller is adapted to control the pressure generating system to deliver the flow of breathing gas to the patient at a second therapy pressure level that is below the peak pressure, the second therapy pressure level being determined during an expiratory phase of the patient, the second therapy pressure level determined based on the determined parameter.

12. The system according to claim 11, wherein the controller is adapted to control the pressure generating system to deliver the flow of breathing gas to the patient at a therapy bi-level pressure support IPAP level during the portion of the inspiratory phase of the patient and deliver the flow of breathing gas to the patient at a therapy bi-level pressure support expiratory positive airway pressure (EPAP) level during at least a portion of an expiratory phase of the patient, wherein the therapy bi-level pressure support IPAP level and EPAP level are determined based on the determined parameter.

13. The system according to claim 11, wherein the controller is adapted to determine the parameter prior to the controlling of the pressure generating system.

14. The system according to claim 11, wherein the parameter is upper airway resistance.

15. The system according to claim 11, wherein the parameter is lung compliance.

16. The system according to claim 11, wherein the lung disease is asthma or COPD.

17. The system according to claim 11, wherein the one or more sensors are operatively coupled to the controller, the one or more sensors being adapted to measure one or more characteristics associated with the flow of breathing gas and to generate one or more signals indicative thereof, wherein the controller is adapted to determine the parameter using the one or more signals.

18. A method of treating lung disease, comprising:
(a) generating, with a pressure support system, a first bi-level positive pressure support for delivery to an airway of a patient at an IPAP/EPAP differential for a first number of respiratory cycles wherein the IPAP/EPAP differential is a pressure determined by subtracting an expiratory positive airway pressure (EPAP) from an inspiratory positive airway pressure (IPAP) for a given respiratory cycle, the IPAP/EPAP differential of the first bi-level positive pressure support being a baseline level based on a predetermined baseline IPAP level and a predetermined baseline EPAP level;

(b) determining, with a controller, a parameter indicative of the patent's pulmonary mechanics, the parameter determination comprising:
  (1) measuring, with one or more sensors, flow responses produced by two different parameter determination IPAP levels delivered to the patient during two successive breaths, subtracting the flow responses from one another, and performing a least squares error fit on flow data that results from the subtraction; or
  (2) randomly varying a level of parameter determination IPAP/EPAP differential delivered to the patient during the two successive breaths, determining a differential volume signal by subtracting volume responses measured during the two successive breaths from one another, and estimating a steady-state response of the differential volume signal;
(c) determining, with the controller, that the determined parameter is outside of a predetermined baseline range;
(d) determining, with the controller, an increase of a predetermined magnitude in the baseline IPAP/EPAP differential to a current IPAP/EPAP differential, wherein the predetermined magnitude of the IPAP/EPAP differential is based on the determined parameter that is indicative of the patient's pulmonary mechanics;
(e) generating, with the pressure support system, a second bi-level positive pressure support for delivery to the airway of the patient at the then current IPAP/EPAP differential for a second number of respiratory cycles;
(f) re-determining, with the controller, the parameter; and
(g) repeating, with the controller and the pressure support system, (d), (e) and (f) one or more times until either it is determined that the then current re-determined parameter is within the baseline range or that the then current IPAP/EPAP differential is equal to a predetermined maximum differential.

19. The method according to claim 18, wherein if it is determined in (g) that the then current IPAP/EPAP differential is equal to the predetermined maximum differential, the method further comprises notifying the patient to begin using asthma medication and continuing to provide the second bi-level positive pressure support at the then current IPAP/EPAP differential.

20. The method according to claim 18, wherein if it is determined in (g) that the then current IPAP/EPAP differential is equal to the predetermined maximum differential, the method further comprises automatically providing asthma medication to the patient while continuing to provide the second bi-level positive pressure support at the then current IPAP/EPAP differential.

21. The method according to claim 18, wherein if it is determined in (g) that the then current re-determined parameter is within the baseline range, the method further comprises: (h) decreasing the then current IPAP/EPAP differential to a decreased level; (i) delivering a third bi-level positive pressure support at the decreased level for a third number of respiratory cycles; (j) re-determining the parameter; and (k) repeating (h), (i) and (j) one or more times until either it is determined that the then current re-determined parameter is outside the baseline range or that the then current decreased level is equal to the baseline level.

22. The method according to claim 21, wherein if it is determined in (k) that the then current re-determined parameter is outside of the baseline range, the method repeats (d), (e), (f) and (g).

23. The method according to claim 21, wherein if it is determined in (k) that the then current re-determined parameter is not outside the baseline range and the then current decreased level is equal to the baseline level, the method further comprises continuing to provide the third bi-level positive pressure support at the baseline level.

24. The method according to claim 18, wherein the lung disease is asthma or COPD.

25. The method according to claim 18, wherein the pressure support system notifies the patient to begin using a medication or automatically provides a medication when the then current IPAP/EPAP differential is equal to a predetermined maximum differential.

* * * * *